United States Patent [19]

Cure

[11] 4,443,118
[45] Apr. 17, 1984

[54] METHOD OF DETERMINING THE CARBON CONTENT OF STEEL MELTS BY THERMAL ANALYSIS

[75] Inventor: Omer P. I. Cure, Diepenbeek, Belgium

[73] Assignee: Electro-Nite Co., Philadelphia, Pa.

[21] Appl. No.: 252,694

[22] Filed: Apr. 9, 1981

[30] Foreign Application Priority Data

Apr. 9, 1980 [DE] Fed. Rep. of Germany ....... 3013621

[51] Int. Cl.³ ............................................ G01N 25/02
[52] U.S. Cl. .................................................... 374/26
[58] Field of Search ............... 73/17 R; 364/497, 557; 374/26

[56] References Cited

U.S. PATENT DOCUMENTS 4,190,888 2/1980 Skurikhin et al. .................... 374/26

Primary Examiner—Herbert Goldstein
Attorney, Agent, or Firm—Seidel, Gonda & Goldhammer

[57] ABSTRACT

The invention relates to a method for determining the carbon content of steel melts by thermal analysis by determining on a cooling curve the arrest point occurring during the liquidis phase change, the carbon content being determined by the arrest point temperature in conjunction with the iron-carbon diagram. In the method, the temperature difference is measured between two arrest points occurring during the liquidus-phase change and a phase transformation and the measured temperature difference is used to determine the carbon content in conjunction with the iron-carbon-diagram.

4 Claims, 3 Drawing Figures

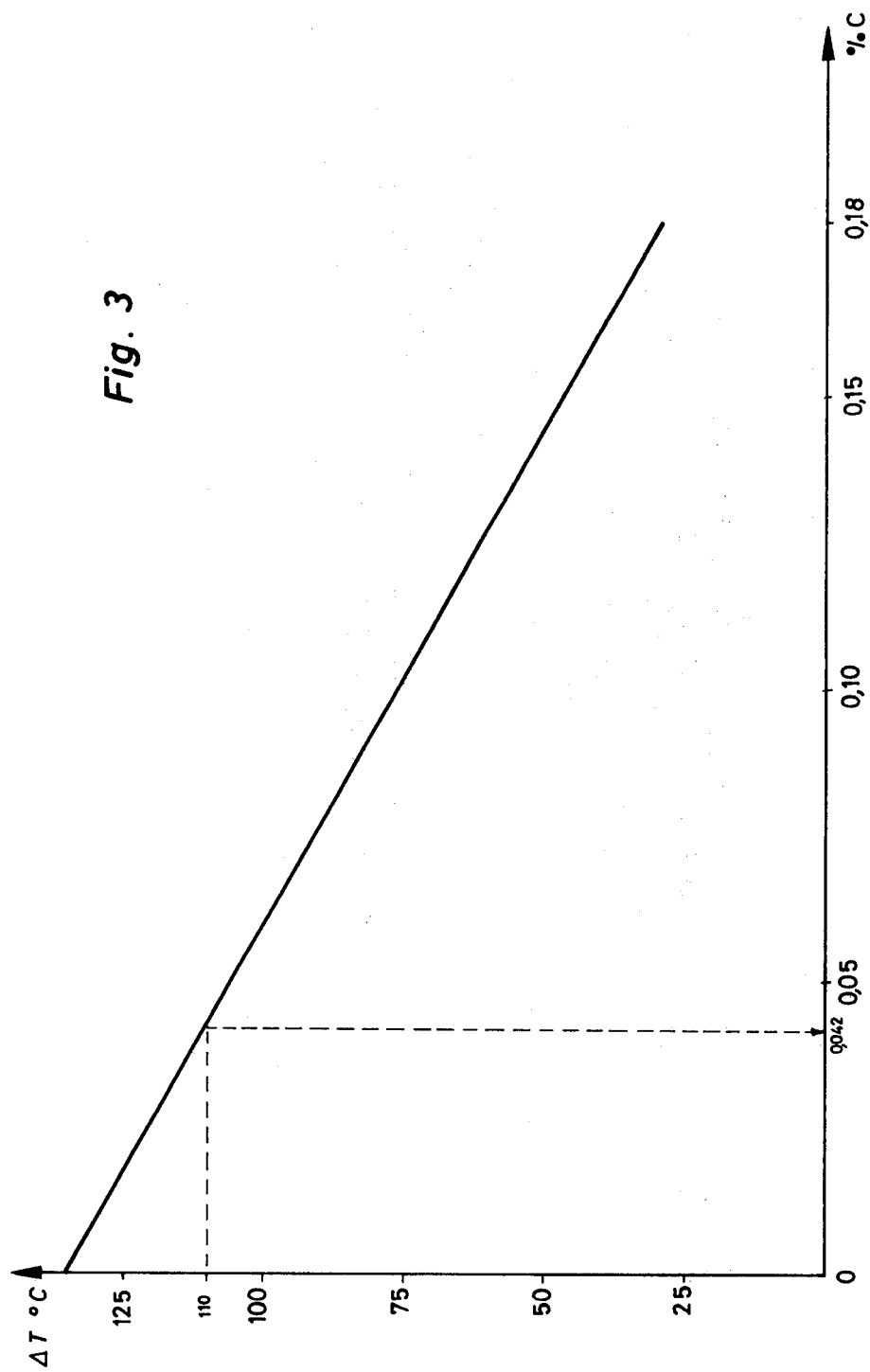

METHOD OF DETERMINING THE CARBON CONTENT OF STEEL MELTS BY THERMAL ANALYSIS

BACKGROUND

The conventional method of determining the carbon content by thermal analysis is to measure the cooling curve. When the temperature falls below the liquidus line (line AB on the FeC diagram) the curve shows a relatively pronounced kink i.e. the "arrest point". The temperature of this "arrest point" is dependent upon the carbon content of the melt which can be determined from existing tables and calibration curves derived from the iron carbon phase diagram.

The known method requires very sensitive accurately calibrated measuring equipment, since a small error in the absolute temperature measurement may result in a large error in the determination of carbon.

SUMMARY OF THE INVENTION

The invention relates to a method for determining the carbon content of steel melts by thermal analysis: by determining on a cooling curve the arrest point temperature occurring at the liquidis phae change; the carbon content being determined by the arrest point temperature in conjunction with the iron carbon phase diagram.

Starting from a method of the initially-described kind, the invention is characterized in that the temperature difference is measured between two arrest points occurring during the liquidus-phase change and the delta-gamma or austenite phase transformation and the measured temperature difference is used to determine the carbon content in conjunction with the iron-carbon phase diagram.

In contrast to the known method, therefore, a differential measurement is made, i.e. the sample is cooled until it passes through a second arrest joint whereby the first point is the liquidus-phase change and the second corresponds to a delta-gamma transformation. The temperature difference on the time-temperature diagram (FIG. 2) between the two arrest points is measured and used to determine the carbon content. The result is a critical advantage in practice, since an absolute temperature measurement requiring exactly calibrated equipment, is not necessary, but only the temperature difference, whereupon the carbon content can be exactly determined.

For the purpose of illustrating the invention, there is shown in the drawings a form which is presently preferred; it being understood, however, that this invention is not limited to the precise arrangements and instrumentalities shown.

The method will be described with reference to an embodiment and the drawings, in which:

FIG. 3 shows a calibration curve.

DETAILED DESCRIPTION

Figure 1:
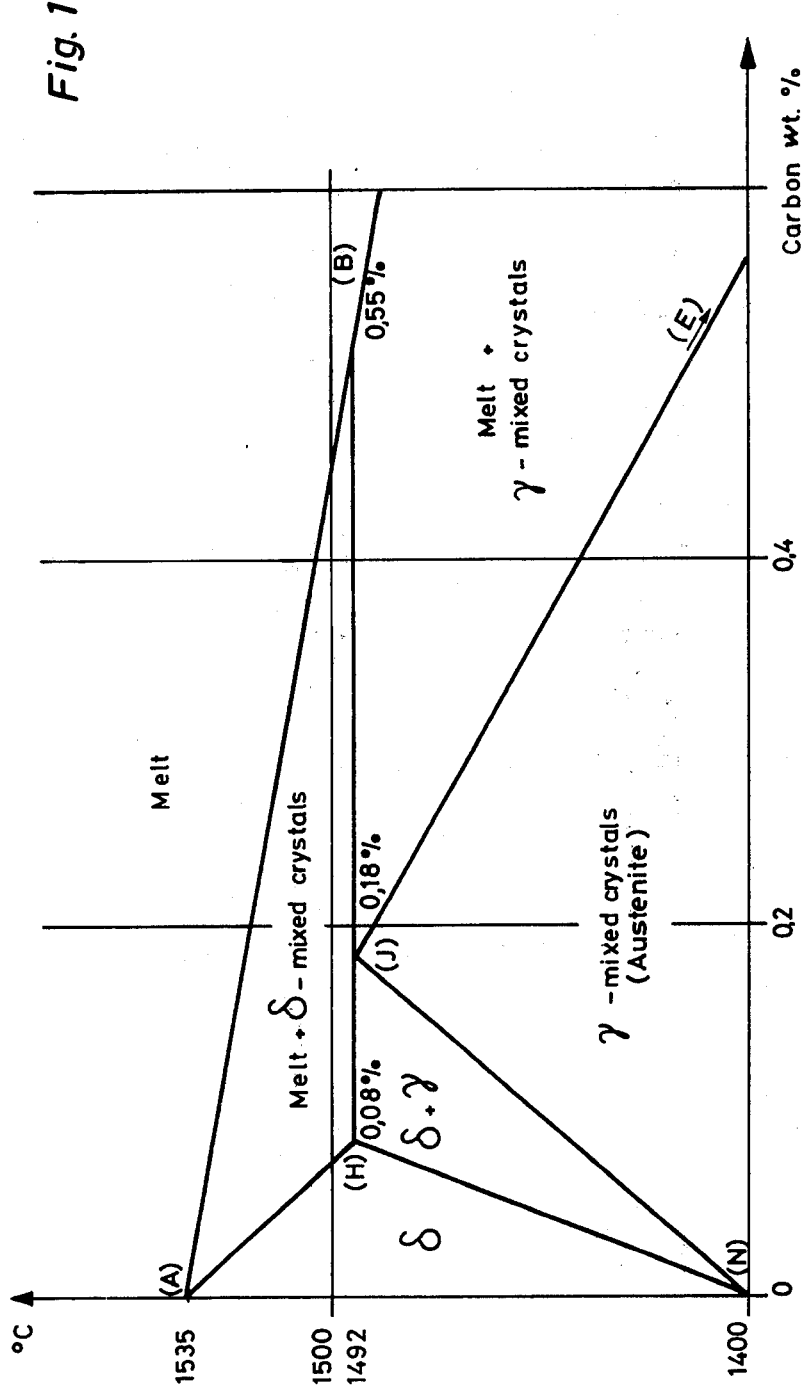
FIG. 1 shows a detail of the iron-carbon diagram in the range from 0 to 0.6% carbon.
Figure 2:
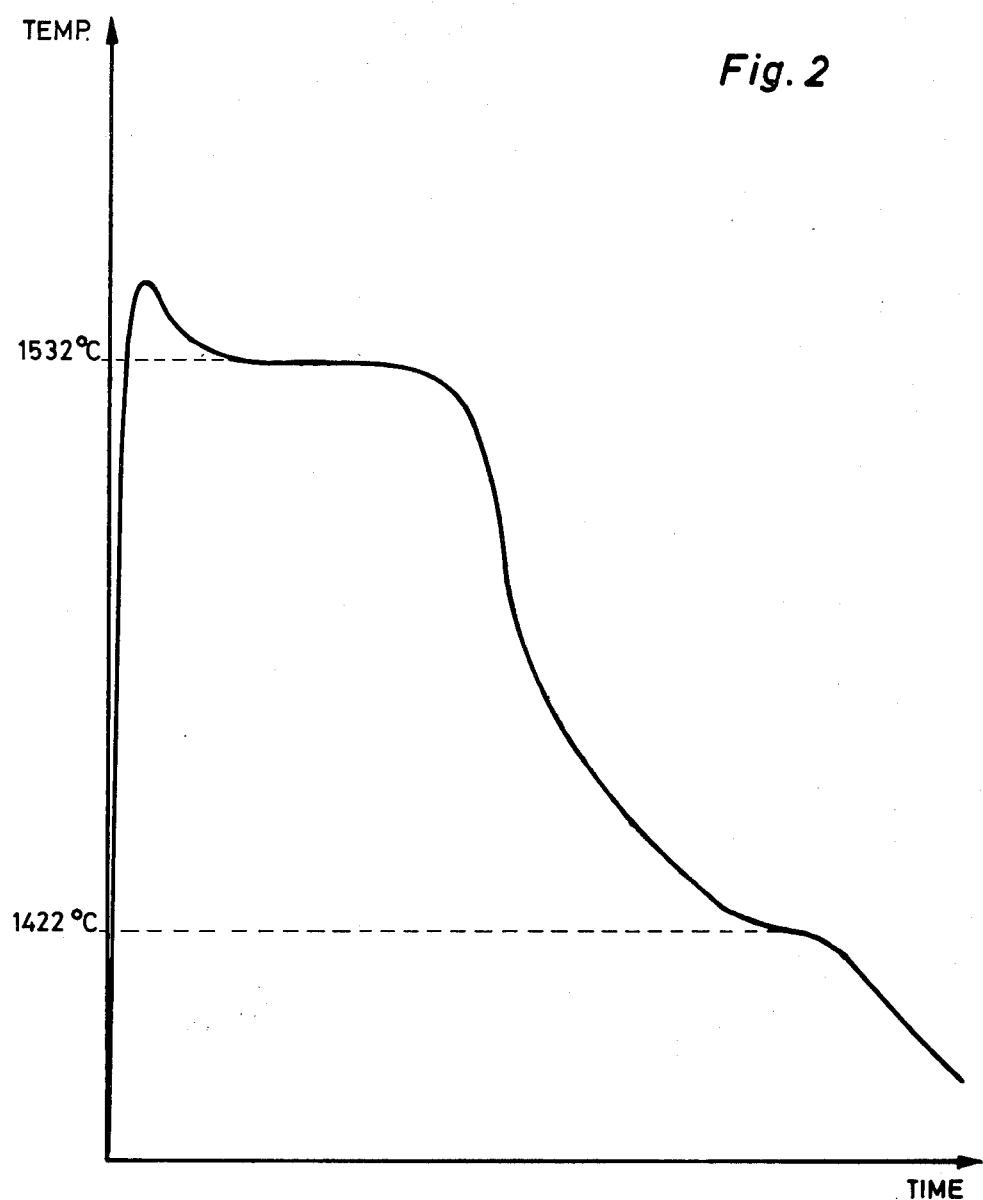
FIG. 2 is a temperature-time diagram.

A sample was taken in conventional manner from a steel melt and thermally analyzed. During cooling, the temperature-time diagram in FIG. 2 was obtained, showing two marked arrest points at 1532° and 1422° C. The measurement is indicated in the iron-carbon diagram in FIG. 1. The first arrest point corresponds to the liquidus temperature whereas the second point corresponds to the delta-gamma phase transformation on passing through the line NH or the austenite phase change on passing through line NJ.

Since lines AB and NJ are straight and satisfy the equation $y = ax + b$, the following equations can be derived for the two measured arrest points:

$$T_1 = -78.2 \cdot C + 1535 \text{ for the liquidus temperature (line AB)}; \quad (1)$$

$$T_t = 511 \cdot C + 1400 \text{ for the phase transformation temperature (line NJ); and} \quad (2)$$

$$\Delta T = -589 \cdot C + 135 \text{ for the difference.} \quad (3)$$

Equation (3) represents the difference between equations (1) and (2). It corresponds to the theoretical relation between the measured temperature difference ($\Delta T$) and the carbon content (C).

In the described example the measured temperature difference was $\Delta T = 110°$ C., based on the measured arrest points. If this value is inserted in equation (3), the carbon content is as follows:

$$C = 25/589 = 0.042\%.$$

As previously pointed out, exactly calibrated instruments are needed for making absolute measurements. In the method according to the invention they are not required, since differences are measured and the two calibration errors cancel out each other.

Another important point is that the relation between the measured temperature $T_1$ and the carbon content C in the known method is represented by equation (1), whereas the relation between the measured difference $\Delta T$ and the carbon content C is given by equation (3). In the first case the directional coefficient is $-78.2$ whereas in the second case it is $-589$, so that carbon can be determined much more accurately by measuring the temperature difference.

In practice, in order to determine carbon from the measurement of temperature differences, it is necessary to make a calibration curve, because the recorded temperatures do not agree exactly with the theoretical values. The reason is that the sample is undercooled and its accumulated heat is released and reduces the rate of cooling and causes an appreciable kink. The measured temperatures are therefore always lower than the theoretical values, the difference being particularly dependent on the cooling rate and thus on the size of sample, thickness of moulds, etc. In order to free the method from dependence on these conditions, a calibration curve is prepared. To this end, a suitable laboratory analysis is made of the carbon content of each sample for which a temperature difference is measured during solidification. These measurements, made in parallel, are plotted as points in a graph in which the temperature difference is the ordinate and carbon is the abscissa.

A calibration curve of the aforementioned kind is shown in FIG. 3 to illustrate the example. It is based on the values in the theoretical equiation (3). A calibration curve prepared in the aforementioned manner for a given measuring probe or a given crucible can be used for very accurately determining the carbon content by measuring the difference according to the invention, irrespective of the absolute values.

The present invention may be embodied in other specific forms without departing from the spirit or essential attributes thereof and, accordingly, reference should be made to the appended claims, rather than to the foregoing specification, as indicating the scope of the invention.

I claim:

1. A method of determining the percentage of carbon in a sample of molten steel by thermal analysis comprising the steps of:
   (a) allowing a sample of molten steel to cool from the liquid phase to the austenite phase,
   (b) determining the temperature of the sample at the liquidus phase change,
   (c) determining the temperature of the sample at the austenite phase transformation,
   (d) comparing said temperatures and ascertaining $\Delta T$,
   (e) using $\Delta T$ to ascertain the percent carbon in said sample.

2. A method in accordance with claim 1 wherein the percent carbon is ascertained by using $\Delta T$ with a calibration of temperature versus percent carbon.

3. A method of determining the percentage of carbon in a sample of molten steel by thermal analysis comprising the steps of:
   (a) allowing a sample of molten steel to cool through the liquidus phase change to the delta-gamma-transformation,
   (b) determining the temperature of the sample at the liquidus phase change,
   (c) determining the temperature of the sample at the delta-gamma-transformation,
   (d) ascertaining $\Delta T$ by comparing said two temperatures,
   (e) using $\Delta T$ to ascertain the percent carbon in said sample.

4. A method in accordance with claim 3 wherein said delta-gamma-transformation temperature is detected while the sample is in the range 1400°–1492° C.

* * * * *